US009939347B2

(12) United States Patent
Xia et al.

(10) Patent No.: US 9,939,347 B2
(45) Date of Patent: Apr. 10, 2018

(54) DISTRIBUTED NONDESTRUCTIVE INSPECTION SYSTEM AND METHOD FOR IDENTIFYING SLICKLINE CABLE DEFECTS AND MECHANICAL STRENGTH DEGRADATION TREND

(71) Applicant: Halliburton Energy Services, Inc., Houston, TX (US)

(72) Inventors: Hua Xia, Huffman, TX (US); Sean Gregory Thomas, Frisco, TX (US); Wei Zhang, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/117,111

(22) PCT Filed: Jul. 22, 2014

(86) PCT No.: PCT/US2014/047612
§ 371 (c)(1),
(2) Date: Aug. 5, 2016

(87) PCT Pub. No.: WO2015/195150
PCT Pub. Date: Dec. 23, 2015

(65) Prior Publication Data
US 2017/0167949 A1 Jun. 15, 2017

Related U.S. Application Data

(63) Continuation-in-part of application No. PCT/US2014/042500, filed on Jun. 16, 2014.

(51) Int. Cl.
*G01J 3/42* (2006.01)
*G01M 11/08* (2006.01)
(Continued)

(52) U.S. Cl.
CPC ......... *G01M 11/086* (2013.01); *E21B 47/123* (2013.01); *G01B 11/16* (2013.01); *G01M 11/31* (2013.01); *G01V 8/10* (2013.01)

(58) Field of Classification Search
CPC .. G01N 33/2823; G01N 21/552; G01N 21/31; G01N 21/33; G01N 21/39;
(Continued)

(56) References Cited

U.S. PATENT DOCUMENTS

| | | |
|---|---|---|
| 2005/0023434 A1 | 2/2005 | Yacoubian et al. |
| 2005/0135763 A1 | 6/2005 | Drenzek et al. |

(Continued)

FOREIGN PATENT DOCUMENTS

| | | |
|---|---|---|
| EP | 2278324 A1 | 1/2011 |
| WO | WO-2014003859 A1 | 1/2014 |

(Continued)

OTHER PUBLICATIONS

"International Application Serial No. PCT/US2014/042500, International Search Report dated Mar. 19, 2015", 4 pgs.
(Continued)

*Primary Examiner* — Michael P Stafira
(74) *Attorney, Agent, or Firm* — Haynes & Boone, LLP

(57) ABSTRACT

Disclosed embodiments include a distributed nondestructive inspection method and system for slickline cable structural defect and mechanical strength degradation inspection. One method may include transmitting a light pulse along an optical fiber embedded in a slickline cable. A reflected light signal is received from the optical fiber in response to the local strain induced refractive index variation. Defects and mechanical strength degradation may be determined by time-dependent time-domain and frequency-domain data analyses of the dynamic strain signals and power spectral density variation as a function of time and cable location.

21 Claims, 6 Drawing Sheets

(51) Int. Cl.
*G01M 11/00* (2006.01)
*G01V 8/10* (2006.01)
*G01B 11/16* (2006.01)
*E21B 47/12* (2012.01)

(58) Field of Classification Search
CPC .......... G01N 21/65; G01N 2021/399; G01N 21/3504; G01N 21/359; G01N 21/6408; G01N 21/85; G01N 2021/317; G01N 21/3577; G01N 2021/1723
See application file for complete search history.

(56) References Cited

U.S. PATENT DOCUMENTS

| | | |
|---|---|---|
| 2009/0157358 A1 | 6/2009 | Kim |
| 2010/0107754 A1* | 5/2010 | Hartog .................. E21B 47/101 73/152.47 |
| 2011/0292763 A1* | 12/2011 | Coates .................... E21B 47/01 367/25 |
| 2012/0170023 A1* | 7/2012 | Szobota ............... G01N 21/552 356/51 |
| 2012/0203493 A1 | 8/2012 | Dobson et al. |
| 2013/0021615 A1* | 1/2013 | Duncan .................. G01H 9/004 356/477 |
| 2013/0342210 A1 | 12/2013 | Stokely |

FOREIGN PATENT DOCUMENTS

| | | |
|---|---|---|
| WO | WO-2015195074 A1 | 12/2015 |
| WO | WO-2015195150 A1 | 12/2015 |

OTHER PUBLICATIONS

"International Application Serial No. PCT/US2014/042500, Written Opinion dated Mar. 19, 2015", 12 pgs.
"International Application Serial No. PCT/US2014/047612, International Search Report dated Mar. 19, 2015", 4 pgs.
"International Application Serial No. PCT/US2014/047612, Written Opinion dated Mar. 19, 2015", 12 pgs.

* cited by examiner

DISTRIBUTED NONDESTRUCTIVE INSPECTION SYSTEM AND METHOD FOR IDENTIFYING SLICKLINE CABLE DEFECTS AND MECHANICAL STRENGTH DEGRADATION TREND

PRIORITY APPLICATIONS

This application is a U.S. National Stage Filing under 35 U.S.C. § 371 from International Application No. PCT/US2014/047612, filed on Jul. 22, 2014, and published as WO 2015/195150 on Dec. 23, 2015, which application claims priority to International Application No. PCT/US2014/042500, filed on Jun. 16, 2014, which applications are incorporated by reference herein in their entirety.

TECHNICAL FIELD

The present embodiments relate to inspection of a downhole wireline cable's structural health condition with distributed sensors. More particularly, the present embodiments relate to a method and apparatus for real-time monitoring of slickline cable structural defects and mechanical strength degradation trend.

BACKGROUND

Various cables (e.g., wireline cable and slickline cable) may be used in a wellbore to provide downhole logging tool support and communication between the downhole environment and the surface of the well. The cable may include communication cabling (e.g., fiber optics, metal conductor wires) between a wireline tool and the surface as well as the structural support to raise and lower the wireline logging tool. However, during use, friction and/or impact between the cable and the wellbore or geological formation may degrade the cable mechanical strength. Subsequently, the various structural defects may propagate along the length of the cable during downhole tool loading or service time. The weight of any logging tool may produce either static tensile stress or transient tensile stress along the slickline cable. Specifically, transient tensile stress events may lead to formation of various internal structural defects, such as cracking and delamination in a polymer composite material based cable. Such structural defects may be localized and may not show obvious influence on cable performance at initial status. However, continuous tensile stress loading may trigger a percolation threshold. The initial nano-structural or micro-structural defects may grow along the loading axis and propagate quickly, resulting in the slickline cable having non-uniform stress loading response.

Conventional nondestructive inspection methods, include laser ultrasonic, transient thermography, microwave, THz-wave, RF, eddy current, or x-ray radiography, used for small-scale structural defects evaluation as a point-inspection technique. Some of these techniques are used during manufacture of slickline cables (e.g., eddy current sensor technique for conductive cable fabrication). Point inspection of slickline cable made from a polymer composite material with reinforced carbon fibers may provide a baseline quality assurance. These techniques may be impractical, however, for analyzing a slickline or wireline cable for inspecting the full length of the cable in an oil field environment.

In addition, manufacturing process-induced structural defects may be too small to be detected. The dynamic loading stress during a downhole tool logging service may facilitate the growth and propagation of different undetected structural defects (e.g., cracks, delamination, voids etc.). Because they provide point-inspection, the above inspection techniques cannot provide a reliable method to effectively scan structural defects along the full length of the cable within a reasonable time for avoiding catastrophic cable failures while in use. There are resulting needs to detect cable structural defects and any mechanical strength degradation trend.

DETAILED DESCRIPTION

Figure 1:
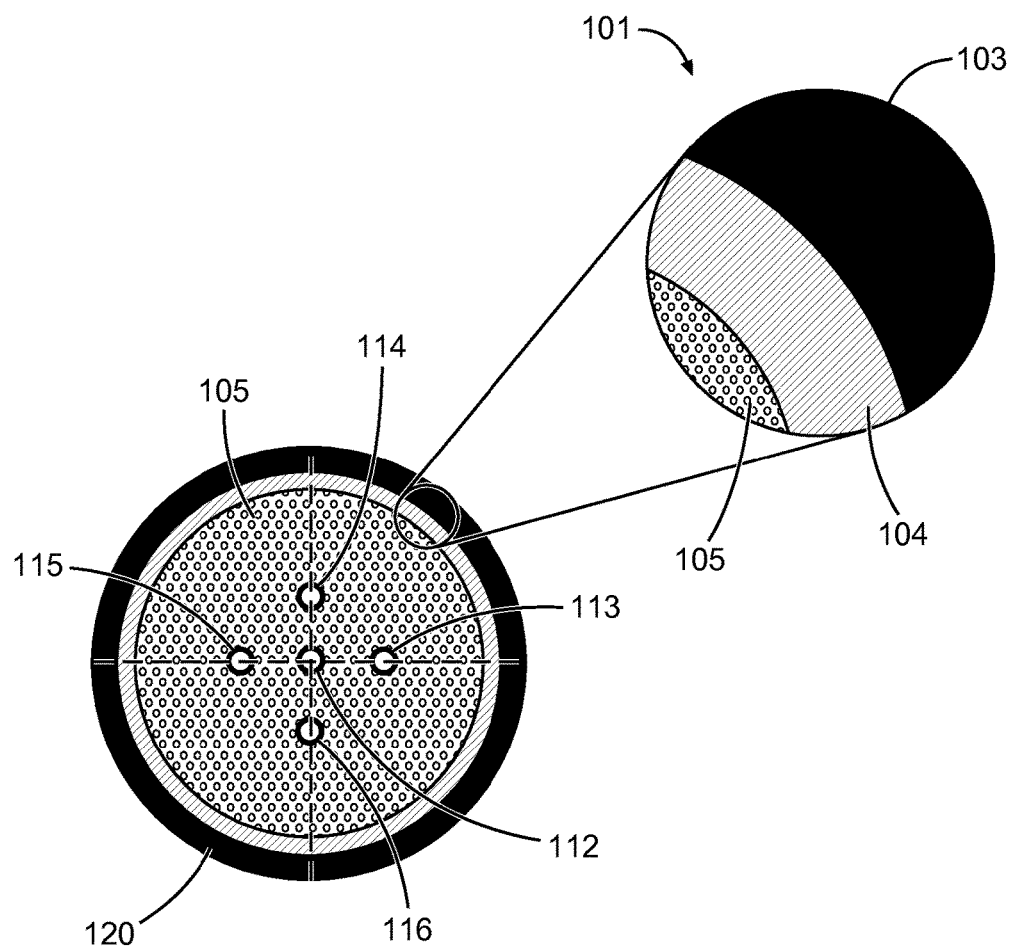
FIG. 1 is a drawing illustrating a cross-sectional view of an embodiment of a polymer composite material based slickline cable with embedded optical fibers.

A slickline or wireline cable may be used to support downhole tools, provide power, and transmit data. In one case, a wireline cable may be metallic wires with an electric conductive core. In another case, a wireline cable may include a combination of electrically conductive wires and optical fibers. Despite the successful use of metallic material based cables in downhole logging services, the weight of the cable itself may limit logging service depth below 20,000 ft because of cable itself will exceed allowed mechanical loading.

Polymer composite materials with embedded reinforcement material (e.g., carbon, glass, ceramic, optical fibers) may be a good candidate for use as a slickline cable. Polymer composite material based cable may provide improved toughness, lower weight, and increased resistance to fatigue and corrosion in comparison to metallic cables. However, polymer composite materials may develop internal structural defects (e.g., fiber or matrix cracking, delamination, voids etc.) at loads far below their failure stress. Such structural defects may not show significant impact on the cable mechanical strength at the initial defect formation stage but the relatively rapid growth and propagation of these structural defects could lead to catastrophic failure events. This is especially true when these cracking and delamination defects grow radially.

Initial nano- or micro-structural defects may be introduced by the manufacturing process and later magnified by transient inhomogeneous loading stress from downhole logging tools. As the downhole logging tool loads on polymer composite material based slickline cable increase, the effective mechanical strength may gradually decrease with repeated loading due to plastic deformation, which depends upon the internal structural defect formation, growth and propagation. The service lifetime of a slickline cable may depend on the orientations of internal structural defect growth and propagation either along axial or radial directions or in-between, and the transient loading induced non-uniform stress often leads to radially grown cracks or delamination defects.

Apparatus, systems, and methods for performing nondestructive, distributed structural defect inspection in slickline cables are presented. A structural defect inspection system may include a light source (e.g., near-infrared), a picosecond gating electronic circuitry, and signal process circuitry.

Coherent Rayleigh scattering is transmitted down a slickline cable in which at least one optical fiber is embedded inside the cable. A scattered, received signal is analyzed in the time-domain. The embedded optical fiber may respond to surrounding strain field variations by strain induced refractive index variations that modulate the scattered light amplitude and phase. Both the cable mechanical strength and its degradation trend may be estimated by the scattered light amplitude and power spectral density. Such a structural defect inspection system may be installed near a wellhead with slickline cable spooling from a reel to the downhole environment.

Transient and non-uniform loading induced structural defects may emit acoustic noises or localized strain waves that are analyzed either in the time-domain or in the frequency-domain by coherent interference techniques that measure coherent light-scattering from optical fiber(s). Structural defects, such as micro-cracking and micro-delamination, may be identified by their modulation on the refractive index of the optical fiber(s). In the time domain, the localized strain field will lead to refractive index change of the fiber core directly, and corresponding phase shift:

$$\in(t) \approx \Delta n/n \approx \Delta\Phi(t)/\Phi;$$

while its Fast Fourier Transform will give power spectral density that could allow one to identify specific spectral signature(s) from structural defects creation process. However, a down-shift of a specific spectral signature in the power spectral density may be associated with slickline cable mechanical strength fatigue or directly with structural defect growth and propagation.

A coupling method is disclosed for using optical fiber(s) to sense structural defect induced acoustic signals that propagate inside the composite cable based acoustic waveguide. For example, a defect may be indicated when a peak strain of the frequency domain power spectral density exceeds a predetermined threshold. The structural defect induced dynamic strain signals may lead to refractive index variations of the optical fiber(s) that are analyzed by the localized strain amplitude, the spectral signature(s) in the power spectral density, and the spectral signature(s) shift trend. Structural defect formation, growth rate, and propagation in the slickline cable may be identified by these parameters. The criteria for identifying slickline cable failure modes may focus on the defect growth rate associated with increasing strain amplitude, acoustic resonant power spectral density, and on potential catastrophic failure event that could be associated with downshift trend of the specific spectral signature(s) in the power spectral density.

Slickline cables may be defined as any cable used to perform wireline operations with a downhole tool in a downhole environment. Such cables may include a polymer composite material based cables or other types of cables in which at least one optical fiber is embedded to perform distributed, nondestructive inspection of structural defects by listening to surrounding acoustic noise signals.

FIG. 1 is a drawing illustrating a cross-sectional view of an embodiment of a polymer composite material based slickline cable with embedded optical fibers. Reference to slickline cables is for purposes of illustration only as the present embodiments may be used to detect defects in any kind of cable capable of transmitting a light signal.

A more detailed cross-sectional view 101 that focuses on the outer layers is also shown. These cross-section views are for purposes of illustration only as other embodiments may include different slickline cable structures.

The detailed view 101 shows a double layered high-acoustic-impedance material that includes a composite material outer protection layer 103 and an inner hard-sheath layer 104. These outer layers 103, 104 may be constructed as an acoustic waveguide 120 for acoustic wave reflection at mismatched impedance interface.

The slickline cable is an acoustic insulated system for optical fibers that monitor internal cable structural defect-induced acoustic noise signals. The surrounding wellbore acoustic noises may be repelled by a high acoustic impedance barrier. To build such an acoustic barrier, a sheath layer 104 may have its longitudinal and shear moduli greater than those of a composite material (e.g., carbon fiber-embedded, polymeric matrix material) 105. The hard-sheath layer 104 may provide a reflection boundary for internal guided acoustic waves. Any external acoustic signals will be reflected from cable surface without noticeable refraction. The hard-sheath layer may be 75% carbon fiber reinforced PEEK with an acoustic impedance of ~15 MRayls. The ratio of the acoustic impedance of outside hard-sheath layer to the internal composite material is at least between 3 and 5.

The optical waveguides are embedded into the polymer composite cable based acoustic waveguide 120 with mechanical coupling provided by a carbon fiber-reinforced polymeric matrix 105. In one embodiment, a slickline cable includes a plurality of single-mode optical fibers 112-116 arranged to easily identify a defect location within the polymeric matrix 105. In another embodiment, at least one optical fiber is embedded inside the polymer matrix.

Figure 3:
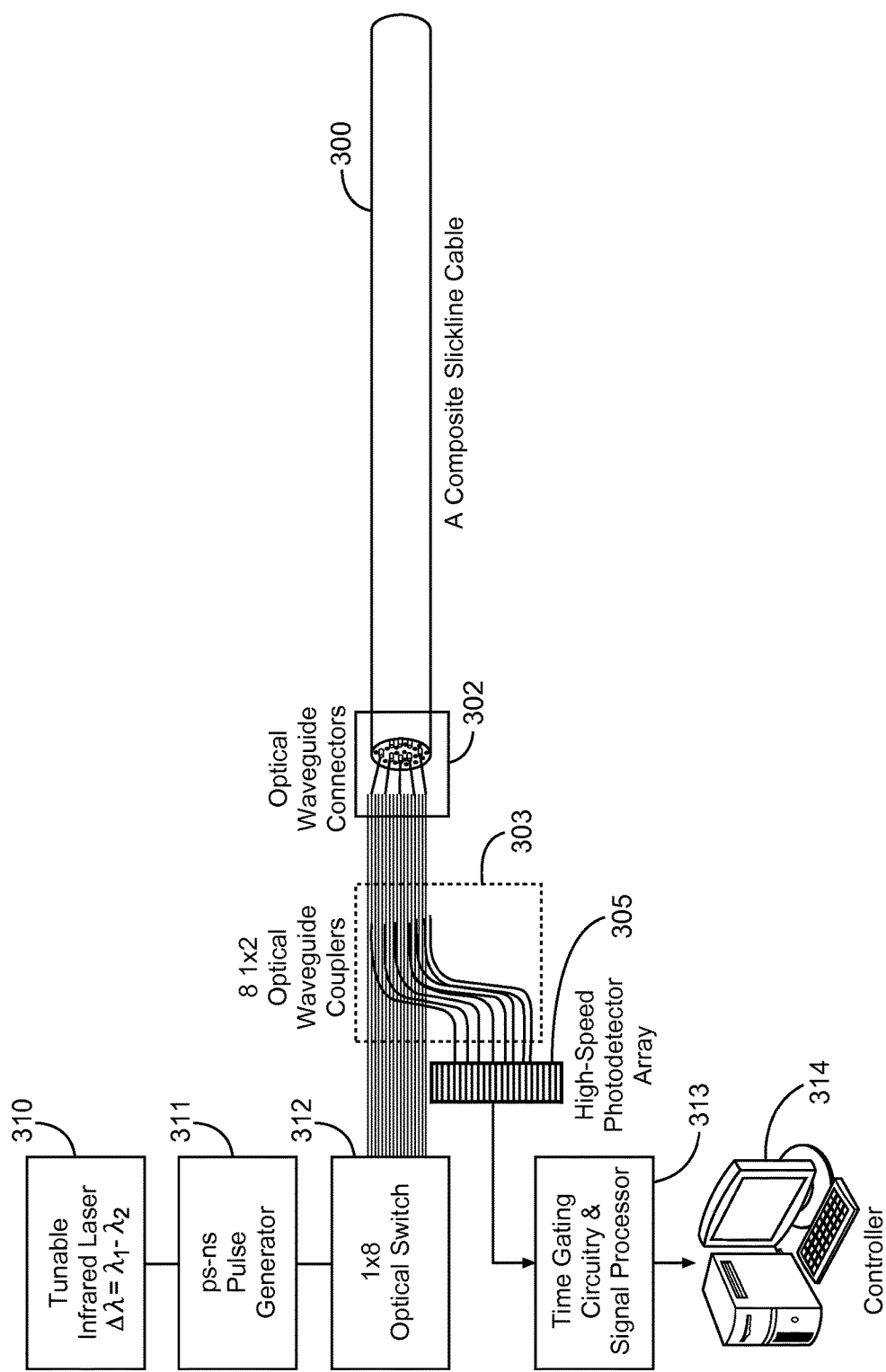
FIG. 3 is a block diagram showing an embodiment of a distributed nondestructive structural defects inspection system.

The measured initial light transmission loss value from each slickline cable is a function of the distance from the downhole environment to the surface system (as seen in FIG. 3). The sum of the measured transmission losses from the optical fibers may be dependent upon optical fiber breakage or localized cable crack induced localized strains.

The manufacturing process may introduce initial nano- or micro-structural defects that may be magnified by transient inhomogeneous loading stress from downhole logging tools. The tensile strain induced defects may be cracks, delaminations, voids, and/or fiber slips with accompanying composite material localized deformation such as bending, torsion, and buckling. The defects may occur below the maximum loading limit of a designed slickline cable. As the downhole logging tool loading on composite material-based slickline cables increases, the effective mechanical strength may be gradually decreased with repeated loading service because of potential plastic deformation that may be attributed to the creation of the structural defects. The induced localized and transient acoustic waves may propagate in opposite directions along an acoustic waveguide as occurred in the slickline cable.

Figure 2:
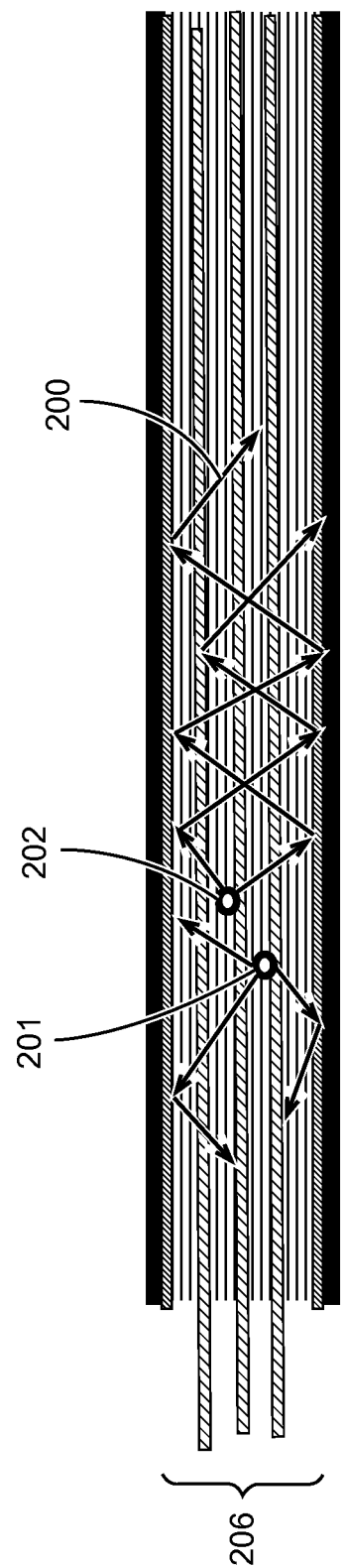
FIG. 2 is a drawing illustrating a cross-sectional view of a slickline cable having localized defect-induced acoustic wave propagation, guided by the acoustic waveguides and picked up by optical fibers.

FIG. 2 is a drawing illustrating a cross-sectional view of a slickline cable having localized defect-induced acoustic wave propagation, guided by the acoustic waveguides and picked up by optical fibers. The slickline cable has localized defect 201, 202 induced broadband acoustic wave propagation 200. The cross-sectional view illustrates multiple acoustic signal detecting lines 206 (e.g., optical fibers) running through the cable. The scattered light from the optical fibers may be used by surface equipment to detect acoustic signals propagated upward or downward through the slickline cable. The localized defects 201, 202 could modify local strain field distribution that changes the refractive index of the optical fibers. When the acoustic impedances of the outside layer 103 and internal fiber-polymer matrix material 105 (see FIG. 1) satisfy guided acoustic wave boundary conditions, the defect formation-induced mechanical strain waves or acoustic waves could propagate along the slickline cable for at least a short distance before attenuated and absorbed by the polymer matrix material 105 (e.g., composite material). In one embodiment a plurality of fibers are arranged in a cross geometry to catch acoustic signals from a specific quadrant in a cable cross section. In another embodiment the measured signal amplitude is used to identify exact location by triangulation method.

A distributed, nondestructive inspection system may provide a coherent light pulse down the slickline cable and receive the reflected, scattered signal back as described subsequently. One embodiment of such a system is illustrated in FIG. 3. Other embodiments may be used to perform the same distributed, nondestructive inspection of slickline cable structural health conditions.

The system of FIG. 3 may use a coherent interference detection technique to detect localized acoustic wave-induced dielectric or refractive index variations as created by defects induced strain waves in the slickline cable 300. The localized refractive index variation will modulate light scattering and the measured dynamic signals could be analyzed in both time-domain and frequency-domain, by a controller 314, as described subsequently.

The system comprises a tunable laser 310 (e.g., infrared) that provides light signals to a picosecond (ps)-nanosecond (ns) pulse generator 311. The laser 310 may provide a coherent light signal in multiple wavelengths that may be used for different lengths of cable. For example, for longer cables, the light signals may be 800 nm to 1000 nm, 1000 nm to 1350 nm, 1500 nm to 1650 nm, or some other wavelength. For shorter cables, the laser 310 may generate a broad band superluminescent signal of 0.5 µm-5 µm. However, the coherent length of a light wave ranges at least 1-3 meters, but it is better to have 5 to 10 meter coherent length.

The ps-ns pulse generator 311 may generate a modulated light pulse signal from the laser signal. The pulse generator may produce a typical pulse width measured in the picoseconds (ps). The modulated light pulse signal from the pulse generator 611 is input to an optical switch 312 (e.g., 1×8) or a multi-channel optical waveguide 303 that may optionally replace the optical switch 312.

For example, the optical switch/multi-channel optical fibers 312/303 provides switching of the modulated light pulse signal amongst a plurality of optical fibers, through optical fiber connectors 302, for using narrow-band laser light source. As discussed and shown previously, the optical fibers are located inside the composite slickline cable 300. In one embodiment, a single-wavelength laser beam is coupled to different optical fibers via a 1×N optical coupler. In another embodiment, the laser beam is coupled to optical fibers by a 1×N optical switch, where N=2, 4, 8, 16, and 32.

A photodetector array 303 is coupled to the optical fiber connectors 302 for receiving the reflected light signals from the optical fibers in the composite slickline cable 300. The optical couplers of the photodetector array 303 convert the received reflected and scattered light signals to electrical signals for use by a time gating circuitry and signal processor 313. The multiple optical signals are picked up with the optical couplers to electronic circuitry that converts optical signal to electronic signal under precise time gating according to a time sequence for signal processing.

The pulsed coherent laser beam is sent to the slickline cable 300 through the optical coupler 303 that also couples back the scattered signal from the cable 300 for coherent elastic scattering light analysis. Since the laser beam propagates at the speed of the light, the scattered signal is gated in the sequence with input pulse time. The intensity of the received, scattered signal is compared with the subsequently received signals from different pulsed signals. Such a signal variation is mainly due to the variation of the refractive index of the fiber core by a local strain effect, $\Delta n(z,t) \propto \Delta \in (r,\phi,z,t)$, where the strain field $\in(r,\phi,z,t)$ may be changed by the creation of local structural defects (e.g., cracks, delaminations, and dislocations). The scattered coherent signal from the slickline cable 300 enables the structural integrity of the composite cable 300 to be real-time monitored along the full length of the cable 300 with a time interval of $\Delta\tau=2*n*L/c \approx 100$ µs, where $c=3\times10^8$ km/s, $n\sim1.46$, and assuming the length, L, of slickline cable is about 10 km. When a periodic time modulated signal with 10 ns as pulse width and 100 µs as duration time, the measured channel signal amplitude, channel phase shift, and frequency signature may be displayed as a function of time.

The refractive index for Rayleigh scattering in optical fibers varies on a microscopic scale, mainly due to density. When the laser light has a length of the coherence, the Rayleigh scattering signal is interfered with from the coherent length of the fiber. The propagated coherent laser beam, similar to a floating interference cavity, may detect local strain field variations caused by local refractive index variations. The refractive index fluctuations give rise to energy loss due to the scattered light, as evidenced by the following coefficient equation:

$$\Delta\alpha = A \cdot (1/\lambda^4) * n^8 \cdot p^2 \cdot k \cdot T \cdot \beta \cdot (\Delta n/n) \qquad \text{Eq.[1]}$$

where A is a constant, n and $\Delta n/n$ is the index of refraction and its relative variation that causes phase shift and intensity changes of the scattered light, p is the photoelastic coefficient of the fiber core, k is the Boltzmann constant, and $\beta$ is the isothermal compressibility. T represents the temperature at which the refractive index fluctuations are "frozen" in the material. It should be pointed out that the relative refractive index change may come from both thermoelastic and strain effects $$\Delta n/n = \beta \cdot \Delta T - (n^2/2E) \cdot \sigma_z \cdot [(1-v) \cdot p_{12} - v \cdot p_{11}], \qquad \text{Eq.[2]}$$

where n is refractive index, $p_{11}$ and $p_{12}$ are photoelastic coefficients, v is Poisson's ratio, and $\sigma_z$ is axial stress on the optical fiber. The first term is from temperature variation induced refractive index change, and second term is due to axial strain or photoelastic effect. Corresponding to transient matrix material medium deformation, the dielectric constant or refractive index of the optical fibers could lead to a phase shift, determined by $$\Delta\Phi/\Phi \cong \Delta n/n. \qquad \text{Eq. [3]}$$

These signal variations may be determined by the controller 314 coupled to the time gating circuitry and signal processing 313. The controller 314 may be a computer, processor, or other control circuitry that may execute instructions representing the embodiments for the method for nondestructive distributed structural defect detection of a slickline cable.

In time-domain data analysis, the local strain variation due to cable operation condition may lead to corresponding changes in the refractive index of an optical fiber core due to a photoelastic effect where thermal induced refractive index change may increase the strain amplitude baseline. However, loading-induced tensile strain or defect formation-induced transient acoustic noises may be related to strain noise variation amplitude with some unique signature characteristics in frequency-domain. The refractive index variation, Δn/n, due to downhole tool loading, could be described by the equation:

$$\Delta n(t)/n \propto \epsilon_{load}(t) + \epsilon_{th} \approx (M+\rho-h) \cdot g/A \cdot E \qquad \text{Eq.[4]}$$

where the $\epsilon_{load}(t)$ term comes from tool loading strain, and $\epsilon_{th}(t)$ term corresponds to thermal induced strain. M is tool mass, ρ is the slickline cable linear density, h is length inside the downhole, g is gravity factor, A is cross section area of the cable, and E is cable Young modulus. Since temperature variation is a slow function in the downhole environment, the dominated strain is from tensile tool loading contribution. As shown in Eq. [4], the tool loading strain could be a linear function of the cable length, with this trend as a baseline data for converting the measured signal to a relative dynamic strain amplitude. When the localized refractive index has been changed by structural defects in the slickline cable, the coherent Rayleigh scattering coefficient is modulated.

In another embodiment, the system may include an acoustic insulated waveguide that isolates surrounding acoustic noises but guides internal defect-induced acoustic wave transmissions inside the slickline cable.

Figure 4:
FIG. 4 is a plot showing an embodiment of a time-domain strain amplitude signal versus cable length.

FIG. 4 is a plot showing an embodiment of a time-domain strain amplitude signal versus cable length. This plot illustrates a time-domain analysis of a local strain amplitude of a length of a cable showing a low strain level along its length. In other words, no anomalous strain or defect is evidenced by the received time-domain strain amplitude signal. Future measured strain amplitudes may be compared to this data as baseline data.

Figure 5:
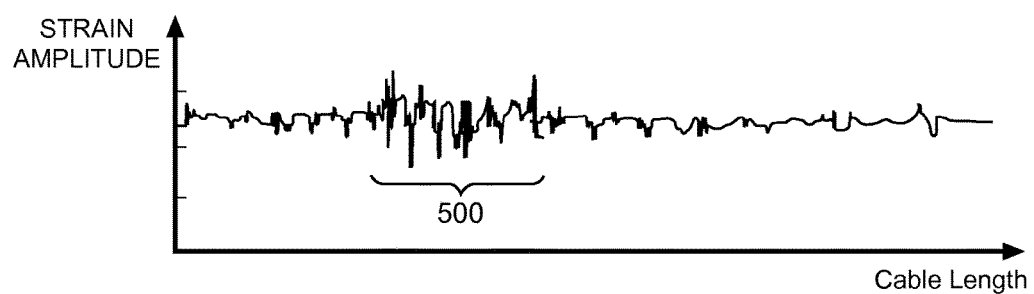
FIG. 5 is a plot showing another embodiment of a time-domain strain amplitude signal versus cable length.

FIG. 5 is a plot showing another embodiment of a time-domain strain amplitude signal versus cable length. This plot illustrates the received anomalous local strain amplitude 500, as compared to the plot of FIG. 4, which may be indicative of a local tensile strain variation or local structural defect.

After the time-domain analysis of the received signal has been performed, a frequency-domain conversion of the time-domain analysis may be performed based on acoustic frequency analysis from the full cable. For example, a Fast Fourier Transform (FFT) algorithm may be used for this conversion, where the specific localized resonant frequency signatures may be identified in the KHz to MHz range. The results of a frequency-domain analysis are illustrated in FIG. 6.

Figure 6:
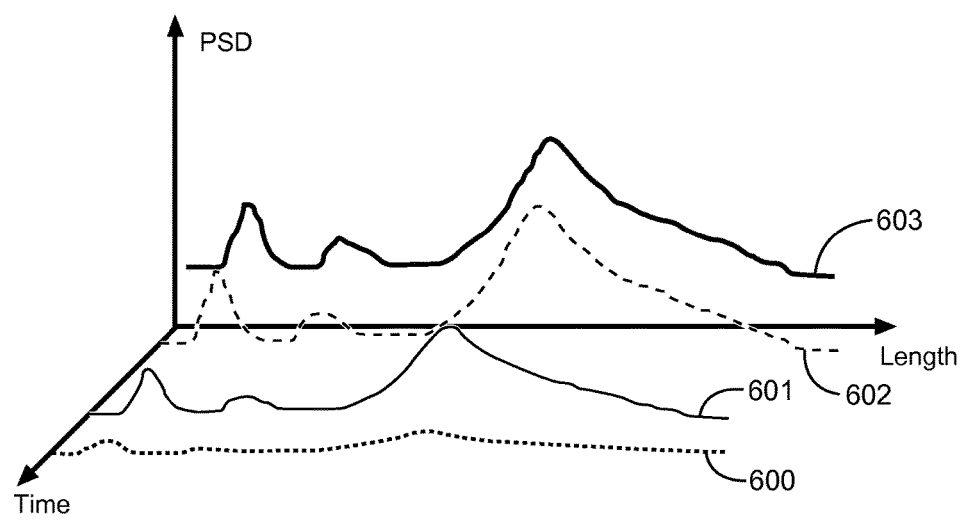
FIG. 6 is a plot showing frequency-domain power spectral density versus cable length.

FIG. 6 is a plot showing frequency-domain power spectral density versus cable length. The frequency-domain power spectral density is along the y-axis versus cable length along the x-axis. A z-axis plot shows a series of plots 600-603 over time.

The conversion from the time-domain analysis to the frequency-domain analysis may aid in real-time monitoring and analysis of the cable defects. Thus, the received time-domain signals of FIGS. 4 and 5 may be more difficult to display, from an instrumentation point of view, than the frequency domain signals of FIG. 6.

Measuring the standard deviation range of the strain amplitude may provide monitoring of the slickline cable operation condition. A pre-calibrated range under specific strain amplitude may be used to evaluate the change between a peak strain amplitude and a predetermined maximum loading strength strain amplitude. A threshold of the peak strain may thus be defined such that a potential slickline cable failure may be determined.

Within the limited coherent length, the resonant frequency power spectral density (PSD) of FIG. 6 may provide a vibrational noise distribution from a section of the slickline cable. Some of signatures of the PSD may be used as a baseline for monitoring long-term cable reliability since tensile loading strain variation may strongly modulate localized cable mechanical response to loading dynamics with a specific power spectral density profile. Some spectral band signals from the observed power spectral density profile may be associated with the wireline tool, reel and mechanical system operation related noises, while other bands may be identified as slickline cable intrinsic signatures.

Since the cable loading may be static or dynamic, the defect formation may also be statistically accumulated from ignorable influence to obvious cable mechanical strength degradation. This time dependent strain amplitude variation rate, γ, may be characterized by the equation:

$$\gamma \propto \Delta \epsilon(t)/\Delta t \qquad \text{Eq.[5]}$$

The fast Fourier Transform (FFT) algorithm may be used to convert the time domain strain amplitude variation to frequency domain analysis by its PSD, where the specific localized resonant frequency signatures may be identified in the KHz to MHz range, which reflects the broad range of the defect size formation process.

The plots of FIG. 6 illustrate potential failure mode analysis method where the increased averaged strain amplitude is accompanied with a decrease in the coherent resonant PSD frequency. The decrease in frequency may be illustrated by the equation:

$$\Delta f(t) = f(t) - f(0) \qquad \text{Eq.[6]}$$

where f(t) is the measured resonant frequency signature value and f(0) is the initial resonant frequency signature value. The negative Δf(t) may reflect cable mechanical strength fatigue that is a result of structural defect creation.

Both the PSD amplitude and acoustic signature frequency plots 600-603 show a decreasing trend with respect to increasing time. Since an acoustic frequency signature may be more reliable way of detecting a slickline cable failure mode, a time-dependent acoustic frequency variation rate, ζ, may be defined by the equation:

$$\zeta \propto \Delta f(t)/\Delta t \qquad \text{Eq.[7]}$$

This variation rate is associated with the structural defect growth. The initial resonant frequency signature value, f(0), could be defined at normal wireline tool loading condition. In practice, the time-dependent strain amplitude variation rate (γ) is combined with the time-dependent frequency variation rate (ζ) to catch a slickline cable failure event during the wireline tool logging operation.

Since the spatial resolution of a coherent Rayleigh based acoustic signal detection is limited to one meter or a few meters, the above time-domain and frequency-domain data analyses may be practically processed sectional cable length by sectional cable length, at least starting from the pulley point to a downhole logging tool end. In one embodiment, the acoustic signal detection may be at a few kHz range to evaluate general cable mechanical strength status across relative large length of the cable. In another embodiment, the acoustic signal detection may be at a few ten kHz ranges to evaluate specific location cable mechanical strength status. In yet another embodiment, a scheme of fast and slow mixing scanning method may be used for cable structural defect detection for catching random defect creation events specifically during upward and downward tool logging processes.

Figure 7:
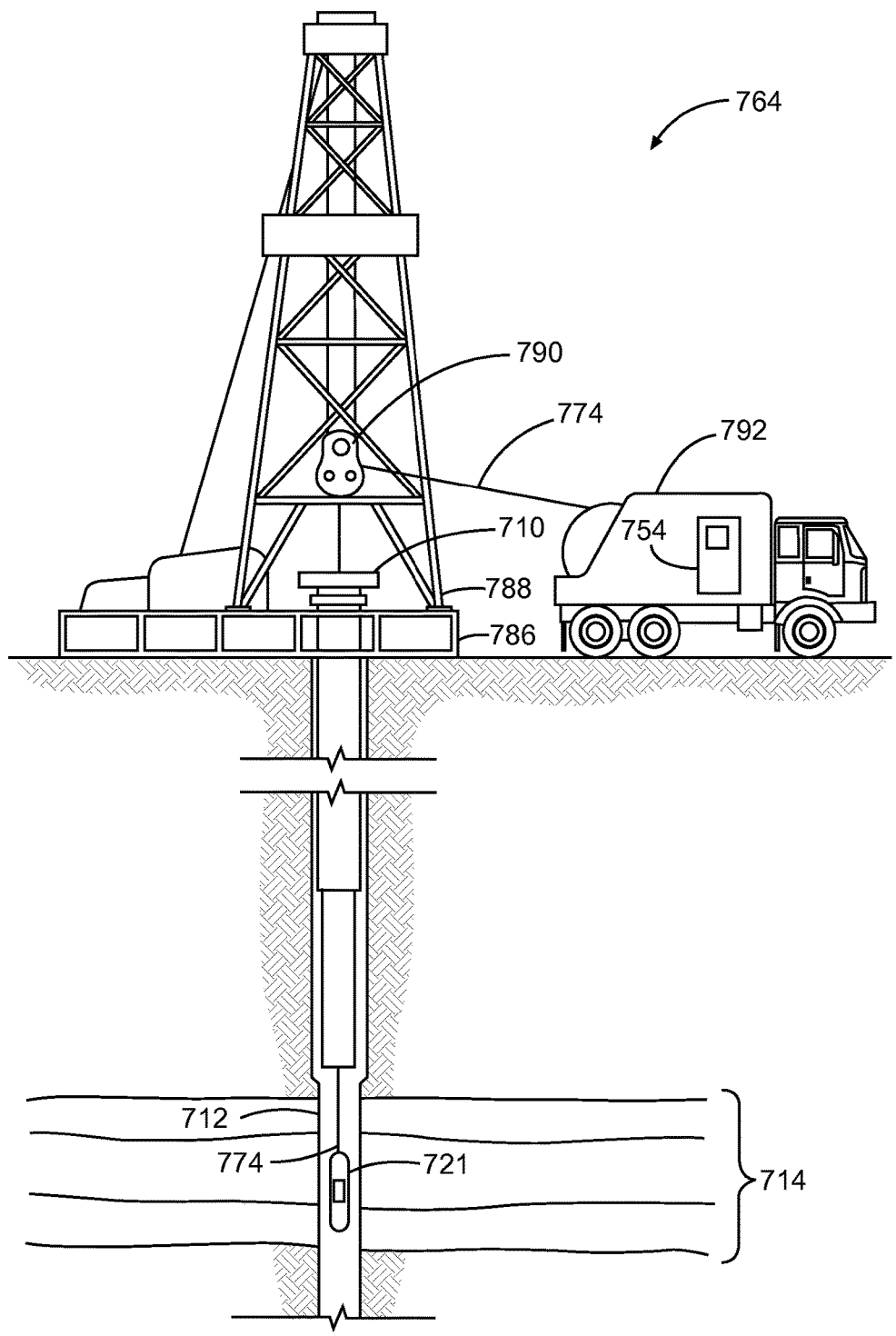
FIG. 7 is a diagram showing an embodiment of a wireline system in accordance with embodiments for distributed, nondestructive defect inspection.

FIG. 7 is a diagram showing an embodiment of a wireline system 764 in accordance with embodiments for distributed, nondestructive defect inspection. The system 764 may include portions of a wireline logging tool body 721, as part of a wireline logging operation. The slickline cable 774 may extend off a cable spool 720 and be coupled to the wireline logging tool body 721.

The optical fiber may comprise carbon and polyimide co-coated pure silica single-mode fibers. Additionally, the slickline cable may comprise a polymer composite material made from fiber reinforced polyphenylene sulfide (PPS) or polyetheretherketone (PEEK) high-performance thermoplastic resins. The polymer composite material may have a high acoustic impedance sheath made from high carbon fiber doped PEEK or PPS configured to guide internal acoustic wave propagation and isolate surrounding acoustic noises. The acoustic impedance ratio of the polymer composite based wireline cable sheath to internal material may be 10 as an ideal acoustic waveguide or acoustic insulator. This will ensure the inspection system only detects cable internal acoustic signals without interference from surrounding downhole machines and noises.

A drilling platform 786 is equipped with a derrick 788 that supports a pulley system 790. Drilling of oil and gas wells is commonly carried out using a string of drill pipes connected together so as to form a drilling string that is lowered through a rotary table 710 into a wellbore or borehole 712. Here it is assumed that the drilling string has been temporarily removed from the borehole 712 to allow a wireline logging tool body 721, such as a probe or sonde, to be lowered by slickline cable 774 into the borehole 712. Typically, the wireline logging tool body 721 is lowered to the bottom of the region of interest and subsequently pulled upward at a substantially constant speed.

During the upward trip, at a series of depths, the instruments (e.g., transducers and receivers) included in the tool body 721 may be used to perform measurements on the subsurface geological formations 714 adjacent the borehole 712 (and the tool body 721). The received data, that may include acoustic data, may be communicated to a surface logging facility 792 for storage, processing, and/or analysis as described previously. The logging facility 792 may be provided with electronic equipment for various types of signal processing.

In some embodiments, the tool body 721 comprises an acoustic tool for obtaining and analyzing acoustic measurements from a subterranean geological formation through a wellbore. The tool is suspended in the wellbore by the slickline cable 774 that connects the tool to a surface control unit 754 as described subsequently. The tool may be deployed in the wellbore on coiled tubing, jointed drill pipe, hard wired drill pipe, or any other suitable deployment technique.

In some embodiments, the slickline cable 774 passes through a packing assembly that isolates downhole high-pressure from surface pressure (not shown in above picture). In addition, the system may include other elements that are used in slickline logging services. Loading strain may be induced from around the pulley section 790 and any transient strain may add static strain as well as loading strain. The tool body 721 may include different downhole sensors or a sampling tester, which may use battery-powered instruments or use casing or the slickline cable 774 as an electrical connection. As a normal operation, the tool body 721 is hanging by the pulley system 790 such that the loading strain is accumulated around the pulley point as a "critical stress turning point" related to cable failures.

Figure 8:
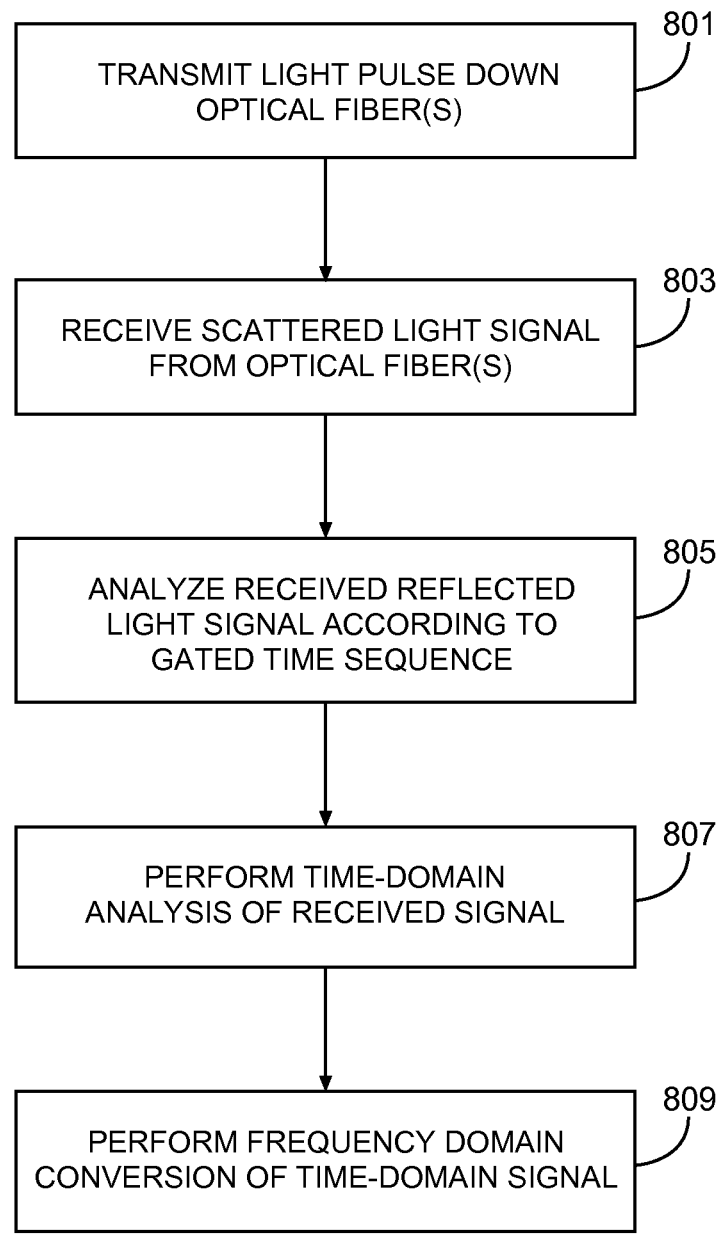
FIG. 8 is a flowchart showing an embodiment of a method for distributed nondestructive defect inspection in a slickline cable.

To monitor the slickline cable operation conditions, the logging facility 792 may include a controller 754, such as a Structural Acoustic-Optical Defect Detection (SADD) System, connected to the slickline cable 774 from the end of the spool cable. The controller 754 may interrogate the tensile strain variation from the full length of the slickline cable, with specific attention on a "critical strain turning point". At such a point, the transient and non-uniform loading induced structural defects could emit reflected light signals, acoustic signals, or localized strain signals that may be analyzed by embodiments of the distributed, nondestructive inspection method for slickline cable structural defect detection. FIG. 8 illustrates one such embodiment.

Structural defects, such as axial and radial cracks and delaminations may be identified by their high-frequency characteristics. The down-shift of the PSD is associated with defects growth and propagation.

FIG. 8 is a flowchart showing an embodiment of a method for distributed nondestructive defect inspection in a slickline cable. The method transmits a light pulse along an optical waveguide 801. A reflected light signal is received (e.g., measured) from the optical waveguide 803. The received reflected signal is analyzed according to a gated time sequence 805 to produce a time-gated signal. A time domain analysis of the time-gated signal may then be performed 807 in order to determine the presence of defects. For example, the defects may be determined based on time-dependent variation rates in scattering intensity, specific spectral signature, PSD, phase shift, strain amplitude, and/or transmission losses of the received reflected signal as compared to the transmitted light pulse. A frequency-domain analysis (e.g., conversion) may be performed on the time-domain signal 809. This may provide the ability to monitor the strain amplitudes in real time.

In the foregoing Detailed Description, it may be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A distributed nondestructive inspection method for identifying structural defects in a cable, the method comprising:

transmitting a light pulse along an optical fiber embedded lengthwise in the cable;

receiving a scattered light signal from the optical fiber, the scattered light signal comprising strain induced refractive index variations;

isolating surrounding acoustic noises with an acoustic insulated waveguide while guiding internal defect-induced acoustic wave transmissions; and analyzing the strain induced refractive index variations to identify structural defects of the cable.

2. The method of claim 1, wherein analyzing the strain induced refractive index variations comprises analyzing a signal amplitude and phase shift of the scattered light signal resulting from structural defect induced acoustic signals.

3. The method of claim 2, wherein analyzing the structural defects in the cable comprises converting a time-domain strain amplitude variation to a frequency-domain power spectral density based on a fast Fourier transform algorithm from time-domain measured strain amplitude.

4. The method of claim 3, wherein analyzing the structural defects in the cable comprises determining when a peak strain of the frequency domain power spectral density exceeds a predetermined threshold.

5. The method of claim 1, further comprising detecting a mechanical degradation trend in the cable by detecting the structural defects in the cable using both time-dependent strain amplitude variation rate and a time-dependent acoustic frequency variation rate.

6. The method of claim 1, further comprising:
determining a baseline time domain strain amplitude signal; and
comparing subsequent time domain strain amplitude signals to the baseline signal.

7. A distributed nondestructive inspection method for detecting slickline cable mechanical strength and mechanical degradation trend, the method comprising:
transmitting a coherent light pulse to an optical fiber embedded lengthwise in the slickline cable;
isolating surrounding acoustic noises with an acoustic insulated waveguide while guiding internal defect-induced acoustic wave transmissions;
measuring a reflected signal from the optical fiber in response to strain induced refractive index variations;
referencing the measured reflected signal according to previous baseline signals; and
analyzing acoustic signal induced time-dependent strain amplitude and frequency shift of the reflected signal to detect structural defects, mechanical strength and degradation trends of the slickline cable.

8. The method of claim 7, wherein transmitting the coherent light pulse comprises a single-wavelength, tunable laser transmitting a light pulse having a coherent length of 1 meter to 10 meters.

9. The method of claim 7, wherein the cable mechanical strength and degradation trend are analyzed by the time-dependent strain amplitude variation, comprising $\Delta\in(t)=\in(t)-\in(0)$ where $\in(t)$ represents a measured strain amplitude and $\in(0)$ represents an initial strain amplitude, and the time-dependent frequency variation, comprising $\Delta f(t)=f(t)-f(0)$ wherein $f(t)$ represents a measured resonant frequency signature value and $f(0)$ represents an initial resonant frequency signal value and the time.

10. A wireline cable nondestructive inspection system comprising:
a wireline cable having at least one optical fiber embedded along its length;
a tunable light source configured to generate a coherent light signal along a length of the optical fiber;
a controller, coupled to the optical fiber, configured to determine structural defects in the wireline cable comprising the optical fiber based on a measured reflected light signal from the wireline cable; and
an acoustic insulated waveguide that isolates surrounding acoustic noises but guides internal defect-induced acoustic wave transmissions inside the wireline cable.

11. The method of claim 7, further comprising determining a baseline dynamic refractive index of the optical fiber from $\Delta n(t)/n \propto \in_{load}(t)+\in_{th}(t)\approx\in(t)$ wherein $\in_{load}(t)$ represents downhole tool loading strain in the slickline cable that represents a baseline strain amplitude due to the slickline cable weight.

12. The method of claim 10, wherein the cable mechanical strength and degradation trend are analyzed by the time-dependent strain amplitude variation rate comprises $\gamma \propto \Delta\in(t)/\Delta t$ and the time-dependent frequency variation rate comprises $\zeta \propto \Delta f(t)/\Delta t$.

13. The system of claim 10, further comprising a pulse generator, coupled to the tunable light source, configured to generate a light pulse in response to the coherent light signal.

14. The system of claim 13, further comprising an optical switch coupling the pulse generator to the optical fibers.

15. The system of claim 10, further comprising time gating circuitry that couples the optical fiber to the controller.

16. The system of claim 15, wherein the time gating circuitry is configured to analyze the reflected light signal according to a gated time sequence.

17. The system of claim 10, further comprising a tool body coupled to the slickline cable.

18. The system of claim 10, wherein the at least one optical fiber comprises carbon and polyimide co-coated pure silica single-mode fibers.

19. The system of claim 10, wherein wireline cable comprises a polymer composite material is made from PPS or PEEK fiber reinforced high-temperature or high-performance thermoplastic resins.

20. The system of claim 19, wherein the polymer composite material has a high acoustic impedance sheath made from high carbon fiber doped PEEK or PPS configured to guide internal acoustic wave propagation and isolate surrounding acoustic noises substantially simultaneously.

21. The system of claim 20, wherein the acoustic impedance ratio of the polymer composite based wireline cable sheath to internal material is in a range of 5-10.

* * * * *